US 11,129,855 B2

(12) United States Patent
Harman, Jr. et al.

(10) Patent No.: US 11,129,855 B2
(45) Date of Patent: *Sep. 28, 2021

(54) METHODS OF PREPARING AND USING NOVEL STEM CELL COMPOSITIONS AND KITS COMPRISING THE SAME

(71) Applicant: VetStem Biopharma, Inc., Poway, CA (US)

(72) Inventors: Robert J. Harman, Jr., Ramona, CA (US); Theodore T. Sand, Poway, CA (US)

(73) Assignee: VetStem Biopharma, Inc., Poway, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/859,790

(22) Filed: Apr. 27, 2020

(65) Prior Publication Data

US 2020/0306317 A1  Oct. 1, 2020

Related U.S. Application Data

(63) Continuation of application No. 15/241,656, filed on Aug. 19, 2016, now Pat. No. 10,668,105, which is a continuation of application No. 10/575,063, filed as application No. PCT/US2004/033220 on Oct. 7, 2004, now Pat. No. 9,453,202.

(60) Provisional application No. 60/510,021, filed on Oct. 8, 2003, provisional application No. 60/510,022, filed on Oct. 8, 2003, provisional application No. 60/509,928, filed on Oct. 8, 2003, provisional application No. 60/510,072, filed on Oct. 8, 2003.

(51) Int. Cl.
  *A61K 35/35* (2015.01)
  *C12N 5/0775* (2010.01)
  *A61K 35/12* (2015.01)

(52) U.S. Cl.
  CPC ............ *A61K 35/35* (2013.01); *C12N 5/0667* (2013.01); *A61K 35/12* (2013.01); *C12N 2509/00* (2013.01); *C12N 2509/10* (2013.01)

(58) Field of Classification Search
  None
  See application file for complete search history.

(56) References Cited

U.S. PATENT DOCUMENTS

| | | |
|---|---|---|
| 4,868,121 A | 9/1989 | Scharp et al. |
| 5,079,160 A | 1/1992 | Lacy et al. |
| 5,143,063 A | 9/1992 | Fellner |
| 5,197,985 A | 3/1993 | Caplan et al. |
| 5,226,914 A | 7/1993 | Caplan et al. |
| 5,322,790 A | 6/1994 | Scharp et al. |
| 5,422,261 A | 6/1995 | Lee et al. |
| 5,424,208 A | 6/1995 | Lee et al. |
| 5,486,359 A | 1/1996 | Caplan et al. |
| 5,744,360 A | 4/1998 | Hu et al. |
| 5,786,207 A | 7/1998 | Katz et al. |
| 5,811,094 A | 9/1998 | Caplan et al. |
| 5,827,735 A | 10/1998 | Young et al. |
| 5,827,740 A | 10/1998 | Pittenger |
| 5,830,510 A | 11/1998 | Petitte et al. |
| 5,837,539 A | 11/1998 | Caplan et al. |
| 5,855,619 A | 1/1999 | Caplan et al. |
| 5,906,934 A | 5/1999 | Grande et al. |
| 5,908,784 A | 6/1999 | Johnstone et al. |
| 5,955,257 A | 9/1999 | Burger et al. |
| 6,010,696 A | 1/2000 | Caplan et al. |
| 6,020,196 A | 2/2000 | Hu et al. |
| 6,022,540 A | 2/2000 | Bruder et al. |
| 6,100,047 A | 8/2000 | Wilkison |
| 6,153,432 A | 11/2000 | Halvorsen et al. |
| 6,171,610 B1 | 1/2001 | Vacanti et al. |
| 6,214,369 B1 | 4/2001 | Grande et al. |
| 6,242,200 B1 | 6/2001 | Wilkison et al. |
| 6,255,112 B1 | 7/2001 | Thiede et al. |
| 6,302,863 B1 | 10/2001 | Tankovich |
| 6,322,784 B1 | 11/2001 | Pittenger et al. |

(Continued)

FOREIGN PATENT DOCUMENTS

| | | |
|---|---|---|
| AU | 2004-213858 B2 | 1/2009 |
| AU | 2009-201915 B1 | 9/2009 |

(Continued)

OTHER PUBLICATIONS

"Clinical Update: Adipose Derived Stem Cells in the Treatment of Equine Soft Tissue and Orthopedic Injuries," Vet-Stem Manuscript published Dec. 2005, 21 pages.
"Inflammation." National Library of Medicine Merriam-Webster Online Medical Dictionary. Online at www.merriam-webster.com/inflammation. Accessed Nov. 23, 2015, 1 page.
"Treatment of Proximal Suspensory Desmitis with Adipose-Derived Regenerative Cells: A Retrospective Study of 54 Cases," Abstract Published 2005, 2 pages.
Awad, H., et al., "Repair of Patellar Tendon Injuries Using a Cell-Collagen Composite," Journal of Orthopaedic Research 21, May 2003, pp. 420-431.

(Continued)

*Primary Examiner* — Robert M Kelly
(74) *Attorney, Agent, or Firm* — Cooley LLP

(57) ABSTRACT

The present invention provides novel stem cell compositions having significant therapeutic and practical advantages, as well as methods of preparing and using such compositions for the treatment and prevention of injury and disease in patients. The invention may be applied to stem cell populations isolated from a wide variety of animals, including humans, and tissues. In particular applications, the invention is used to prepare a stem cell composition from a collagen-based tissue, such as adipose tissue, isolated from a patient, and the stem cell composition is subsequently provided to a site of actual or potential injury in the patient. The invention further includes related kits comprising the stem cell compositions, which are remarkably stable and retain viability and efficacy during storage and shipment.

24 Claims, No Drawings

(56) References Cited

U.S. PATENT DOCUMENTS

| | | |
|---|---|---|
| 6,355,239 B1 | 3/2002 | Bruder et al. |
| 6,387,367 B1 | 5/2002 | Davis-Sproul et al. |
| 6,391,297 B1 | 5/2002 | Halvorsen |
| 6,391,348 B1 | 5/2002 | Stilborn et al. |
| 6,429,013 B1 | 8/2002 | Halvorsen et al. |
| 6,482,231 B1 | 11/2002 | Abatangelo et al. |
| 6,492,130 B1 | 12/2002 | Wilkison et al. |
| 6,541,024 B1 | 4/2003 | Kadiyala et al. |
| 6,555,374 B1 | 4/2003 | Gimble et al. |
| 6,569,633 B1 | 5/2003 | Wilkison et al. |
| 6,589,728 B2 | 7/2003 | Csete et al. |
| 6,607,498 B2 | 8/2003 | Eshel |
| 6,610,535 B1 | 8/2003 | Lu et al. |
| 6,630,154 B1 | 10/2003 | Fraker et al. |
| 6,709,864 B1 | 3/2004 | Pittenger et al. |
| 6,767,738 B1 | 7/2004 | Gage et al. |
| 6,777,231 B1 | 8/2004 | Katz et al. |
| 6,849,255 B2 | 2/2005 | Gazit et al. |
| 7,429,488 B2 | 9/2008 | Fraser et al. |
| 7,470,537 B2 | 12/2008 | Hedrick et al. |
| 9,453,202 B2 * | 9/2016 | Harman, Jr. ............ A61P 9/10 |
| 10,668,105 B2 * | 6/2020 | Harman, Jr. ............ A61P 25/00 |
| 2001/0033834 A1 | 10/2001 | Wilkison et al. |
| 2002/0005205 A1 | 1/2002 | Barry et al. |
| 2002/0039572 A1 | 4/2002 | Downs |
| 2002/0076400 A1 | 6/2002 | Katz et al. |
| 2002/0106353 A1 | 8/2002 | Wood et al. |
| 2002/0115647 A1 | 8/2002 | Halvorsen et al. |
| 2002/0119126 A1 | 8/2002 | Halvorsen |
| 2002/0128592 A1 | 9/2002 | Eshel |
| 2002/0155096 A1 | 10/2002 | Chancellor et al. |
| 2002/0197241 A1 | 12/2002 | Boss et al. |
| 2003/0031695 A1 | 2/2003 | Kadiyala et al. |
| 2003/0054331 A1 | 3/2003 | Fraser et al. |
| 2003/0082152 A1 | 5/2003 | Hedrick et al. |
| 2003/0118566 A1 | 6/2003 | Neuman et al. |
| 2003/0124721 A1 | 7/2003 | Cheatham et al. |
| 2003/0161816 A1 | 8/2003 | Fraser et al. |
| 2003/0161818 A1 | 8/2003 | Weiss et al. |
| 2003/0166278 A1 | 9/2003 | Gimble et al. |
| 2003/0185807 A1 | 10/2003 | Gazit et al. |
| 2003/0202966 A1 | 10/2003 | Prockop et al. |
| 2003/0203483 A1 | 10/2003 | Seshi |
| 2004/0009157 A1 | 1/2004 | Gazit et al. |
| 2004/0018174 A1 | 1/2004 | Palasis |
| 2004/0022787 A1 | 2/2004 | Cohen |
| 2004/0033214 A1 | 2/2004 | Young et al. |
| 2004/0037810 A1 | 2/2004 | Von Heimburg et al. |
| 2004/0067218 A1 | 4/2004 | Casteilla et al. |
| 2004/0067219 A1 | 4/2004 | Vida |
| 2004/0092011 A1 | 5/2004 | Wilkison et al. |
| 2004/0096431 A1 | 5/2004 | Fraser et al. |
| 2004/0097867 A1 | 5/2004 | Fraser et al. |
| 2004/0106196 A1 | 6/2004 | Fraser et al. |
| 2004/0107453 A1 | 6/2004 | Furcht et al. |
| 2004/0136967 A1 | 7/2004 | Weiss et al. |
| 2004/0151706 A1 | 8/2004 | Shakhov et al. |
| 2004/0152190 A1 | 8/2004 | Sumita |
| 2004/0166097 A1 | 8/2004 | Prockop et al. |
| 2004/0259948 A1 | 12/2004 | Tontonoz |
| 2005/0008626 A1 | 1/2005 | Fraser et al. |
| 2005/0076396 A1 | 4/2005 | Katz et al. |
| 2005/0260174 A1 | 11/2005 | Fraser et al. |
| 2007/0274960 A1 | 11/2007 | Harman et al. |
| 2010/0317671 A1 | 12/2010 | Chen |
| 2012/0052049 A1 | 3/2012 | Woods et al. |
| 2015/0044166 A1 | 2/2015 | Riddle, Jr. |
| 2015/0147409 A1 | 5/2015 | March et al. |
| 2017/0196912 A1 | 7/2017 | Harman, Jr. et al. |
| 2018/0353549 A1 | 12/2018 | Harman |
| 2019/0255120 A1 | 8/2019 | Harman et al. |

FOREIGN PATENT DOCUMENTS

| | | |
|---|---|---|
| WO | WO 1996-028539 A1 | 9/1996 |
| WO | WO 1998-017791 A1 | 4/1998 |
| WO | WO 1998-032450 A1 | 7/1998 |
| WO | WO 2000-044882 A2 | 8/2000 |
| WO | WO 2000-053795 A1 | 8/2000 |
| WO | WO 2001-062901 A2 | 8/2001 |
| WO | WO 2001-080865 A2 | 11/2001 |
| WO | WO 2003-010243 A2 | 2/2003 |
| WO | WO 2003-022988 A2 | 3/2003 |
| WO | WO 2003-024215 A1 | 3/2003 |
| WO | WO 2003-053346 A2 | 7/2003 |
| WO | WO 2003-080801 A2 | 10/2003 |
| WO | WO 2004-022078 A1 | 3/2004 |
| WO | WO 2004-072273 A1 | 8/2004 |
| WO | WO 2004-074457 A2 | 9/2004 |
| WO | WO 2005-035742 A2 | 4/2005 |
| WO | WO 2010-020005 A1 | 2/2010 |
| WO | WO 2014-203268 A2 | 12/2014 |

OTHER PUBLICATIONS

Black et al., "Effect of Adipose-Derived Mesenchymal Stem and Regenerative Cells on Lameness in Dogs with Chronic Osteoarthritis of the Coxofemeral Joints: A Randomized, Double-Blinded, Multicenter, Controlled Trial," Veterinary Therapeutics 8(4):272-284, 2007.

Black et al., "Effect of Intraarticular Injection of Autologous Adipose-Derived Mesenchymal Stem and Regenerative Cells on Clinical Signs of Chronic Osteoarthritis of the Elbow Joint in Dogs," Veterinary Therapeutics 9(3):192-200, 2008.

Boquest et al., "Isolation and Transcription Profiling of Purified Uncultured Human Stromal Cells: Alteration of Gene Expression after In Vitro Cell Culture," Molecular Biology of the Cell 16:1131-1141, 2005.

Brown, S., et al., "Adipose-Derived Stem Therapy for Severe Muscle Tears in Working German Shepherds: Two case reports," Stem Cell Discovery, vol. 2, No. 2, 2012, pp. 41-44.

Brunstedt et al., "Isolation of Islets from Mice and Rats," in Methods in Diabetes Research, V. 1, Laboratory Methods, Lamer, J. and Pohl, S.L. (eds.), Wiley-Interscience, New York, 1985, pp. 245-258.

Butrick CW. 2003. Interstitial Cystitis and Chronic Pelvic Pain: New Insights in Neuropathology, Diagnosis, and Treatment. Clin Obstet Gyn 46: 811-823.

Folch J et al. 1957. A simple method for the isolation and purification of total lipids from animal tissues. J Biol Chem 226: 497-509.

Garcia-Olmo et al., "Treatment of enterocutaneous fistula in Crohn's Disease with adipose-derived stem cells: a comparison of protocols with and without cell expansion," Int J Colorectal Dis 24:27-30, 2009.

Gimble, JM, et al., "Adipose Tissue-Derived Therapeutics," Cell & Tissue Based Therapy, Expert Opin. Biol. Ther., Aug. 2003, 3(5), pp. 705-713.

Gimble, JM, et al., "Adipose-Derived Adult Stem Cells: Isolation, Characterization, and Differentiation Potential," Cytopherapy, Jan. 2003, vol. 5, No. 5, pp. 362-369.

Hamudikuwanda et al., "Adipose tissue progesterone concentrations in dairy cows during late pregnancy and early lactation," Animal Reproduction Science 43:15-23, 1996.

Hauner, H., et al., "Promoting Effect of Glucocorticoids on the Differentiation of Human Adipocyte Precursor Cells Cultured in a Chemically Defined Medium," Glucocorticoids and Human Preadipose Cell Differentiation, 84(5), Nov. 1989, pp. 1663-1670.

Herthel, D., "Enhanced Suspensory Ligament Healing in 100 Horses by Stem Cells and Other Bone Marrow Components," Proceedings of the Annual Convention of the AAEP, vol. 47, pp. 319-321, 2001.

Jorgensen C et al. 2003. Engineering mesenchymal stem cells for immunotherapy. Gene Therap 10: 928-931.

Luyten, F., "Mesenchyma Stem Cells in Osteoarthritis," Osteoarthritis, pp. 599-603, 2004.

(56) References Cited

OTHER PUBLICATIONS

Meredith, C., et al., "Adipose Derived Stem Cell Therapy in the Treatment of Canine Degenerative Joint Disease Secondary to Conformational Abnormalities," Manuscript Published 2005, 3 pages.
Meredith, T., et al., "A Review of Adipose Derived Stem Cell Science and Clinical Application in Equine Practice," Abstract from Meeting Published 2006, 6 pages.
Mitchell, K., et al., "Matrix Cells from Wharton's Jelly Form Neurons and Glia", Stem Cells, Jan. 21, 2003; pp. 50-60.
Mizuno, H., et al., "Myogenic Differentiation by Human Processed Lipoaspirate Cells," Plastic and Reconstructive Surgery, Jan. 2002, pp. 199-209.
Murphy, J., et al., "Stem Cell Therapy in a Caprine Model of Osteoarthritis," Arthritis and Rheumatism, vol. 48, No. 12, Dec. 2003, pp. 3464-3474.
Nathan, S., et al., "Cell-Based Therapy in the Repair of Osteochondral Defects: A Novel Use of Adipose Tissue," Tissue Engineering, vol. 9, No. 4, pp. 773-749, 2003.
Nixon et al., "Effect of adipose-derived nucleated cell fractions on tendon repair in horses with collagenase-induced tendinitis," Am J Vet Res 69(7):928-937, 2008 (2008).
Rich, F., et al., "Single-Center Study of 83 Horses with Suspensory Injuries Treated with Adipose-Derived Stem and Regenerative Cells," Stem Cell Discovery, vol. 4, 2014, pp. 44-53.
Riordan, N., et al., "Non-Expanded Adipose Stromal Vascular Fraction Cell Therapy for Multiple Sclerosis," Journal of Translational Medicine, vol. 7, No. 29, 2009, p. 1-9.
Rodbell, M., "Metabolism of Isolated Fat Cells: I. Effects of Hormones on Glucose Metabolism and Lipolysis," Journal of Biological Chemistry, 239:2, 1964, 375-380.
Rodbell, M., "Metabolism of Isolated Fat Cells: V. Preparation of "Ghosts" and Their Properties; Adenyl Cyclase and Other Enzymes," Journal of Biological Chemistry, 242:24, 1667, 5744-5750.
Smith RKW et al. 2003. Isolation and implantation of autologous, Equine Veterinary Journal, 4 pages.
Soda et al., "Adipocyte Stem Cell: A Brief Review," International Journal of Cell Cloning 1(2):79-84, 1983.
Tholpady, S.S. et al., "Mesenchymal Stem Cells from Rat Visceral Fat Exhibit Multipotential Differentiation In Vitro," The Anatomical Record Part A 272A, Mar. 2003 pp. 398-402.
Traktuev et al., "A Population of Multipotent CD34-Positive Adipose Stromal Cells Share Pericyte and Mesenchymal Surface Markers, Reside in a Periendothelial Location, and Stabilize Endothelial Networks," Circ Res. 102:77-85, 2008.
Van et al., "Complete Differentiation of Adipocyte Precursors. A Culture System for Studying the Cellular Nature of Adipose Tissue," Cell and Tissue Research 195(2):317-329, 1978.
Van, R., et al., "Cytological and Enzymological Characterization of Adult Human Adipocyte Precursors in Culture," The Journal of Clinical Investigation, vol. 58, Sep. 1979, pp. 699-704.
Varma et al., "Phenotypical and functional characterization of freshly isolated adipose tissue-derived stem cells," Stem Cells Dev. 16(1):91-104, 2007.
Wabitsch, M. et al., "IGF-1- and IGFBP-3-Expression in Cultured Human Preadipocytes and Adipocytes," Horm Metab Res 32, Nov. 2000, pp. 555-559.
Wickham, M., et al., "Multipotent Stromal Cells Derived from the Infrapatellar Fat Pad of the Knee," Clinical Orthopaedics and Related Research, No. 412, pp. 196-212, Jul. 2003.
Winter, A., et al., "Cartilage-Like Gene Expression in Differentiated Human Stem Cell Spheroids," Arthritis & Rheumatism, vol. 48, No. 2, Feb. 2003, pp. 418-429.
Yoshimura et al., "Characterization of freshly isolated and cultured cells derived from the fatty and fluid portions of liposuction aspirates," J Cell Physiol. 208(1):64-76, 2006.
Zhu et al., "The effect of age on osteogenic, adipogenic and proliferative potential of female adipose-derived stem cells," J Tissue Eng Regen Med 3:290-301, 2009.
Zilberfarb, V., et al., Human Immortalized Brown Adipocytes Express Functional β3-Adrenoceptor Coupled to Lipolysis, Journal of Cell Science, 110, Apr. 1997, pp. 801-807.
Zuk et al., "Multilineage Cells from Human Adipose Tissue: Implications for Cell-Based Therapies," Tissue Engineering 7(2):211-228, 2001.
Zuk, P. et al., "Human Adipose Tissue is a Source of Multipotent Stem Cells," Molecular Biology of the Cell, The American Society for Cell Biology, vol. 13, Dec. 2002, pp. 4279-4295.
Blaber et al., "Analysis of in vitro secretion profiles from adipose-derived cell populations," Journal of Translational Medicine 2012, 10:172, 16 pages.
Kemper et al., "Treatment of smoke inhalation in five horses," J. Am Vet Med Assoc. Jan. 1, 1993; 202(1):91-94.
Birks EK, Shuler KM, Soma LR, Martin BB, Marconato L, Del Piero F, et al. EIPH: postrace endoscopic evaluation of Standardbreds and Thoroughbreds. Equine Vet J Suppl. 2002:375-378.
Derksen et al., "A Exercise-induced pulmonary hemorrhage in horses: the role of pulmonary veins.,"Compendium Continuing Education for Veterianarians. 33(4):E1-E6 (2011).
Hinchcliff KW, Couetil LL, Knight PK, Morley PS, Robinson NE, Sweeney CR, et al. Exercise induced pulmonary hemorrhage in horses: American College of Veterinary Internal Medicine consensus statement. J Vet Intern Med. 29:743-758 (2015).
Kindig CA, McDonough P, Fenton G, Poole DC and Erickson HH. Efficacy of nasal strip and furosemide in mitigating EIPH in Thoroughbred horses. J Appl Physiol 91:1396-400 (2001).
Manohar Mand Goetz TE. Pulmonary vascular pressures of exercising thoroughbred horses with and without endoscopic evidence of EIPH. J Appl Physiol 81:1589-93 (1996), downloaded from http://jap.physiology.org/by 10.220.33.5 on Apr. 3, 2017.
Sullivan S. and Hinchcliff K, "Update on exercise-induced pulmonary hemorrhage," Vet Clin North Am Equine Pract. 31:187-198 (2015).
Sullivan SL, Anderson GA, Morley PS and Hinchcliff KW. Prospective study of the association between exercise-induced pulmonary haemorrhage and long-term performance in Thoroughbred racehorses. Equine Vet J. 2015; 47:350-357.
Michelotto et al., "Pulmonary inflammation due to exercise-induced pulmonary haemorrhage in Thoroughbred colts during race training," The Veterinary Journal 190:E3-E6 (2011).
Morris ME, Beare JE, Reed RM, Dale JR, LeBlanc AJ, Kaufman CL, et al. Systemically delivered adipose stromal vascular fraction cells disseminate to peripheral artery walls and reduce vasomotor tone through a CD11b+ cell-dependent mechanism. Stem Cells Transl Med. 2015; 4:369-80.
Rigotti G, Marchi A, Galie M, Baroni G, Benati D, KramperaM, et al. Clinical treatment of radiotherapy tissue damage by lipoaspirate transplant: a healing process mediated by adiposederived adult stem cells. Plast Reconstr Surg. 2007; 119:1409-1422; discussion 23-24.
Hinchcliff et al., "Tracheobronchoscopic assessment of exercise-induced pulmonary hemorrhage in horses," Am J Vet Res. 2005; 66:596-598.
Schaffler et al. "Concise Review: Adipose Tissue-Derived Stromal Cells-Basic and Clinical Implications for Novel Cell-Based Therapies," Stem Cells 25:818-827 (2007).
Nemeth et al., "The N-terminus of hepcidin is essential for its interaction with ferroportin: structure-function study," Blood 107:328-333 (2006).
Agrahari et al., "How are we improving the delivery to back of the eye? Advances and Challenges of Novel Therapeutic Approaches," Expert Opinion on Drug Delivery 14(10):1145-1162 (2017).
Caplan et al., "The MSC: An Injury Drugstore," Cell Stem 9:11-15 (2011).
Cooper et al., "Immunobiological Barriers to Xenotransplantation," International Journal of Surgery 23:211-216 (2015).
Dib et al., "Cell Therapy for Cardiovascular Disease: A Comparison of Methods of Delivery," J. of Cardiovasc. Trans. Res., 4:177-181 (2011).
Harman et al., "A Prospective, Randomized, Masked, and Placebo-Controlled Efficacy Study of Intraarticular Allogeneic Adipose Stem Cells for the Treatment of Osteoarthritis in Dogs," Frontiers in Veterinary Science 3(81), pp. 1-10 (2016).

(56) References Cited

OTHER PUBLICATIONS

Ikehara et al., "Grand Challenges in Stem Cell Treatments," Frontier in Cell and Developmental Biology 1(2):1-2 (2013).
Li et al., SARS-CoV-s triggers inflammatory responses and cell death through caspase-8 activation, Signal Transduction and Targeted Therapy 5(235), pp. 1-10 (2020).
Liu et al., "The Immunogenicity and Immune Tolerance of Pluripotent Stem Cell Derivatives," Frontiers in Immunology 8(645):1-6 (2017).
Ikonomou et al., "Unproven Stem Cell Treatments for Lung Disease—An Emerging Public Health Problem," Am J Respir Crit Care Med 195:13-14 (2017).
Meirelles et al., "Mechanisms involved in the therapeutic properties of mesenchymal stem cells," Cytokine & Growth Factor Reviews 20 (2009) 419-427.
Meneghin et al., "Infectious disease, the innate immune response, and fibrosis," J Clin Invest. 117(3):530-538 (2007).
Murphy et al., "Mesenchymal stem cells: environmentally responsive therapeutics for regenerative medicine," Experimental & Molecular Medicine 45, e54, pp. 1-16 (2013).
Namdev et al., "Challenges and Approaches for Oral Protein and Peptide Drug Delivery," Research J. Pharm. and Tech. 9(3)305-312 (2016).
Noble et al., "Pulmonary Fibrosis: Patterns and Perpetrators," The Journal of Clinical Investigation 122(8):2756-2762 (2012).
Rehman et al., "Delivery of Therapeutic Proteins: Challenges and Strategies," Current Drug Targets 17:1172-1188 (2016).
Singer et al., "Mesenchymal Stem Cells: Mechanisms of Inflammation," Annu. Rev. Pathol. Mech. Dis. 6:457-78 (2011).
Sorento Outcomes Press Release, dated Jan. 31, 2021, 2 pages.
Sorento Outcomes Press Release, dated Jan. 27, 2021, 2 pages.
Study of Intravenous Administration of Allogeneic Adipose Stem Cells for COVID-19—Tabular View—ClinicalTrials.gov, dated Feb. 2, 2021, 7 pages.
Venkataraman et al., "Overactive Epidermal Growth Factor Receptor Signaling Leads to Increased Fibrosis after Severe Acute Respiratory Syndrome Coronavirus Infection," Journal of Virology 91(12)e00182, pp. 1-17—(2017).
Wu et al., "Cell Delivery in Cardiac Regenerative Therapy," Aging Research reviews 11:32-40 (2012).
Zheng et al., "Treatment of acute respiratory distress syndrome with allogeneic adipose-derived mesenchymal stem cells: a randomized, placebo-controlled pilot study," Respiratory Research 15:39, pp. 1-10 (2014).

\* cited by examiner

METHODS OF PREPARING AND USING NOVEL STEM CELL COMPOSITIONS AND KITS COMPRISING THE SAME

CROSS-REFERENCE TO RELATED APPLICATION(S)

This application is a Continuation of U.S. application Ser. No. 15/241,656, filed Aug. 19, 2016, now U.S. Pat. No. 10,668,105, which is a Continuation of U.S. application Ser. No. 10/575,063, filed Feb. 1, 2007, now U.S. Pat. No. 9,453,202; which is a National Stage of International Application No. PCT/US2004/033220 filed on Oct. 7, 2004, which claims the benefit under 35 U.S.C. § 119(e) of U.S. Provisional Patent Application No. 60/510,021 filed Oct. 8, 2003; U.S. Provisional Patent Application No. 60/510,022 filed Oct. 8, 2003; U.S. Provisional Patent Application No. 60/509,928 filed Oct. 8, 2003; and U.S. Provisional Patent Application No. 60/510,072 filed Oct. 8, 2003, where these applications are incorporated herein by reference in their entireties.

BACKGROUND OF THE INVENTION

Field of the Invention

The present invention is generally related to the field of stem cell-based therapy and, more specifically, to compositions comprising stem cells and methods of preparing and using compositions comprising stem cells for the treatment and prevention of injury and disease.

Description of the Related Art

Due to their remarkable ability to regenerate and develop into a variety of cell types, stem cells possess great therapeutic potential in the treatment of a wide variety of diseases and injuries, particular those involving the destruction or damage of normal tissue, such as spinal cord injuries, Parkinson's Disease, Alzheimer's Disease, and multiple sclerosis. Until fairly recently, it was thought that multipotent stem cells could only be isolated from embryonic tissue. However, it has now been discovered that multipotent stem cells exist in a variety of adult tissues, including bone marrow, skin, brain, muscle and adipose tissue. This discovery has sparked increased interest in stem cell-based therapies, since such adult stem cells are more readily available than embryonic stem cells, and their use does not raise the same ethical concerns.

One significant limitation to the therapeutic use of stem cells is that they are present in very low numbers in most adult tissues, and their isolation and purification is a tedious and expensive process. The generally practiced method of preparing stem cells before providing them to a patient involves purifying cells from a tissue sample, isolating stem cells, e.g., using antibodies specific to stem cell surface markers from other cells, and/or culturing the cells. In addition, many procedures further involve treating the cells with an agent that induces differentiation down a specific lineage. The reagents used for the purification, culturing and differentiation of stem cells are very expensive, thus limiting the availability of stem cell-based therapies. In addition, the procedures involved in preparing and storing stem cells can result in cell death and loss of function, thus reducing the number of useful stem cells isolated and limiting their ability to be stored and shipped prior to use.

Clearly, there is a need in the art for improved methods of preparing stem cell populations suitable for therapeutic and prophylactic use, including methods capable of purifying a high number of viable cells from a tissue sample, particularly for autologous uses, which may be performed with increased ease and reduced costs. In addition, there is a related need for methods of preparing purified stem cells from a patient's tissue sample obtained by a medical professional, and providing the purified cells to a medical professional for administration to the patient. The present invention meets these needs by providing novel methods of preparing stem cell populations, novel compositions comprising stem cells, and streamlined procedures for preparing and providing stem cells for delivery to a patient.

BRIEF SUMMARY OF THE INVENTION

The present invention provides improved methods of preparing stem cells, improved compositions comprising stem cell populations, improved methods of treating and preventing injury or disease using the stem cell compositions, and kits comprising stem cell compositions.

In one embodiment, the invention includes a method of preparing a purified cell population comprising stem cells for introducing into a patient, comprising obtaining adipose tissue from said patient, processing said adipose tissue to separate cells therein from other tissue components, and purifying the separated cells from other tissue components.

In a related embodiment, the invention provides a method of preparing a composition comprising purified adipose tissue-derived stem cells for introducing into an animal, comprising obtaining adipose tissue from the tail head region of said animal, processing said adipose tissue to separate cells therein from other tissue components, and purifying the separated cells from other tissue components.

In another embodiment, the invention includes a method of providing a composition comprising purified stem cells for introducing into a patient, comprising processing collagen-based tissue obtained from a patient to separate cells therein from other tissue components, purifying the separated cells, and placing said separated cells in a container, thereby providing a composition comprising purified stem cells. In particular embodiment, the container is a syringe, vial, or cryovial.

In a further embodiment, the invention includes a method of preparing a purified cell population comprising collagen-based tissue-derived stem cells for delivery to a patient, comprising obtaining collagen-based tissue from said patient, processing said collagen-based tissue to separate cells therein from other tissue components, and purifying the separated cells, wherein said processing comprises contacting said collagen-based tissue with a series of screens, thereby preparing a purified cell population comprising collagen-based tissue-derived stem cells. In a further embodiment, the processing also includes treating the tissue with an enzyme that facilitates the release of cells from other tissue components.

In yet another related embodiment, the invention provides a method of preparing a purified cell population comprising collagen-based tissue-derived stem cells for providing to a patient, comprising obtaining collagen-based tissue from said patient and processing said collagen-based tissue to isolate cells therein from other tissue components, wherein said processing comprises contacting the tissue with a surface to which the tissue adheres, thereby preparing a purified cell population comprising collagen-based tissue-derived stem cells. In a further embodiment, the processing also comprises mincing said tissue and/or treating the tissue with an enzyme that facilitates the release of cells from other tissue components. In one embodiment, contacting comprises mixing the tissue with particles of the adherent surface.

In particular embodiments encompassing a surface to which the tissue adheres, the surface is Velcro, polystyrene, glass fiber, glass wool, cellulose, or ceramic.

In a related embodiment, the invention includes a device adapted for preparing a cell population comprising collagen-based tissue-derived stem cells, comprising a series of mesh screens, arrayed such that one or more of the screens may be separated from each other while in contact with collagen-based tissue sample. In one embodiment, the screens comprise edges capable of cutting an adipose tissue sample. In another embodiment, the device comprises a cutting implement that may be inserted between adjacent screens. In a further embodiment, the device further includes a container comprising said mesh screens, which may include an opening though which an adipose tissue sample may be placed into said container.

In a variety of embodiments, methods of the invention further include suspending prepared cells in a physiologically compatible solution, and/or freezing or lyophilizing the cells.

In other embodiments, the methods further comprise shipping cells and compositions to a physician or veterinarian.

In particular embodiments of the invention, the collagen-based tissue is adipose tissue or umbilical cord matrix.

In certain embodiments, methods of preparing a cell population or composition comprising stem cells further comprise suspending said purified cells in a physiologically compatible buffer, placing said purified cells in a syringe, and/or freezing cells in freezing medium.

In particular embodiments, methods of preparing a cell population or composition comprising stem cells do not include isolating stem cells from other purified cells.

In related embodiments, methods of processing tissue include mincing the adipose tissue, treating the adipose tissue with an enzyme that facilitates the release of cells from other tissue components, exposing the adipose tissue to ultrasonic energy; and/or treating the adipose tissue with perflurocarbons. In one embodiment, enzyme treatment is performed at a temperature below 28° C. and/or a pH below 7.0.

The invention further includes a method of treating an injury or disease in a patient, comprising providing to said patient an isolated cell population or composition comprising collagen-based tissue-derived stem cells prepared according to a method of the invention.

Similarly, the invention includes a method of preventing an injury in a patient, comprising providing to said patient an isolated cell population or composition comprising collagen-based tissue-derived stem cells prepared according to a method of the invention.

In particular embodiments, the injury or disease is a musculo-skeletal injury or disease. In certain embodiment, the injury is a sprain, strain, dislocation, bruising, tear, or fracture. In other embodiments, the injury or disease is an ischemic injury or disease or a septic injury or disease. In various embodiments, the tissue is tendon, ligament, cartilage, or bone; hoof laminae; or lung, blood vessels, liver, nerve, or heart.

In certain embodiments, the isolated cell population or composition is provided directly to a site of injury or disease. In another embodiment, the isolated cell population or composition is provided to the bloodstream of said patient. In one embodiment, the isolated cell population or composition is provided by injection, intravenously or interarterially.

In related embodiments, the methods of the invention are practiced on a variety of different animals. Accordingly, in various embodiments, cell populations are prepared from tissue isolated from any animal (including patients and donors), cell populations include cells prepared from tissue from any animal, and methods of treatment are performed on any animal. Accordingly, in particular embodiments, a patient or animal is a human, a non-human animal, a horse or camel, a dog or cat, an exotic or zoological animal, a hoofed mammal, a bird, or a cow or goat. In various embodiments, the invention is practiced on patients or animals having significant commercial value, such as performance or racing animals, zoo animals, livestock or farm animals, dairy animals, companion animals, and rare or exotic animals.

In certain embodiments, tissue is obtained from any of a variety of sites on a patient or donor, including the tail head region. In other embodiments, tissue is a collagen-based tissue.

In various embodiments, compositions and cell populations, which comprise stem cells, further comprise one or more additional cellular or non-cellular tissue component. In one embodiment, additional cells are blood cells, white blood cells, fibroblasts, fibroblast-like cells, neutrophils, monocyte/macrophages, and/or basophils. In another embodiment, additional tissue components are extracellular matrix polypeptides or fragments thereof, proteoglycans, cytokines, or growth factors. In one embodiment, an extracellular matrix polypeptide is collagen, thrombospondin, fibronectin, vitronectin, cytotactin, laminin or an integrin.

In additional embodiments, the invention further includes kits comprising a cell population or composition of the invention. In one embodiment, the invention provides a kit useful in the treatment of an injury or disease in an animal, comprising: a container comprising a composition comprising a stem cell population purified from a collagen-based tissue obtained from an animal.

In a related embodiment, the invention includes a kit useful in the prevention of an injury in an animal, comprising: a container comprising a composition comprising a stem cell population purified from a collagen-based tissue obtained from an animal.

In yet another related embodiment, the kit comprises two or more containers, each comprising a composition comprising a stem cell population purified from a collagen-based tissue obtained from an animal.

In one embodiment, a kit is useful in the treatment or prevention of a musculo-skeletal tissue injury.

In another kit embodiment, the stem cell population is present in a physiologically compatible solution. In various related embodiments, the container is a syringe, a vial, or a cryovial. In further embodiments, the composition is frozen or lyophilized.

In certain kit embodiments, the collagen-based tissue was obtained from the animal to be treated. In one embodiment, the collagen-based tissue is adipose tissue obtained from the tail head region of the animal. In other embodiment, the tissue is tendon, ligament, cartilage, or bone. In yet another embodiment, the tissue is lung tissue, blood vessels, liver, nerve, and heart. In another embodiment, the tissue is hoof laminae.

DETAILED DESCRIPTION OF THE INVENTION

The present invention provides novel and improved methods of preparing stem cells useful for the therapeutic and prophylactic treatment of injuries and diseases. The invention further includes cell populations and compositions comprising stem cells purified according to such methods. The invention is based, in part, upon the surprising discovery that stem cell populations purified according to the methods of the invention have increased efficacy and increased stability as compared to stem cells purified using previous methods, which typically include one or more additional steps of isolating stem cells from other cells present in a tissue source and/or culturing or differentiating the isolated stem cells prior to administration to a patient. Accordingly, the invention provides methods of preparing a stem cell population that are simpler and more convenient to perform than prior methods. Furthermore, the invention includes methods related to the preparation of convenient-to-use stem cell compositions that can be supplied in an applicator, such as a syringe, for administration to a patient.

A. Methods of Purifying Stem Cells

In general, the basic method of the invention includes processing a tissue sample comprising stem cells to separate cells therein from other tissue components and purifying the separated cells from other tissue components. In certain embodiments, the method does not include one or more of the steps of isolating stem cells from other purified cells, culturing the purified cells, or differentiating the purified cells. In other embodiments, a method of the invention further comprises one or more of these steps. The invention may be used to isolate stem cells from any tissue source, including but not limited to adipose tissue, umbilical cord matrix, brain tissue, blood, muscle, bone marrow, tooth tissue and skin. In one embodiment, the tissue is a collagen-based tissue, such as adipose tissue or umbilical cord matrix. The methods of the invention are particularly well-suited to processing collagen-based tissues to facilitate the release of stem cells.

Tissue may be obtained from humans and other animals. In one embodiment, the animal is a mammal. In certain embodiments, tissue is obtained from animals having significant commercial or economic value, such as horses, dogs, cats, camels, and cows. Similarly, in other embodiments, the tissue is obtained from performance or sport animals, such as horses and dogs. In other embodiments, tissue is obtained from a companion animal, such as a dog or cat. In a further embodiment, tissue is obtained from exotic dogs (wolves, jackals, dingos, etc.) and exotic cats (leopard, fisher cat, mountain lion, jagarundi, tiger, lion, cheetah, etc.). In other embodiments, tissue is obtained from exotic or zoological animal, including but not limited to hoof stock, including ungulates or hoofed mammals, including, e.g., gazelle, buffalo, rhinoceros, eland, etc. In another embodiment, a tissue sample is obtained from a high value exotic species, including but not limited to birds, including, e.g., parrots, macaws, etc. In certain embodiments, tissue is obtained from large exotic or zoological animals, including but not limited to, zebras, lions, tigers, elephants, rhinoceroses, hippopotamuses, bears, and giraffes.

Tissue may be obtained from fetuses, or juvenile or adult animals, including humans. Furthermore, tissue may be obtained from the patient to whom the purified cells will be provided, or, alternatively, tissue may be obtained from a donor and the purified cells provided to a different patient. As such, the invention contemplates both autologous and allogeneic uses of the purified cells.

Tissue may be isolated from a patient or donor by any means available in the art. In certain embodiments, tissue is isolated by lipoaspiration, surgical removal, withdrawal using a needle and syringe, or lipectomy. A variety of additional procedures are described in U.S. Patent Application Publication No. 2003/0161816 A1 and U.S. Pat. Nos. 6,020,196 and 5,744,360. Furthermore, tissue may be isolated from any suitable location on an animal, depending upon the type of tissue being isolated. For example, adipose tissue may be isolated from locations including, but not limited to, the tail head, the omentum or other abdominal location, subcutaneously, the stomach, hips or thighs. As used herein, the tail head region is the general area from the midline lateral and cranial to the insertion of the tail into the body of the animal, extending forward to the area of the loin and the points of the hips. Umbilical cord matrix is typically isolated from the matrix within the umbilical cord, otherwise referred to as Wharton's jelly.

Of particular interest is the use of adipose tissue obtained during surgical procedures, and especially procedures that relate to the spaying and neutering of animals such as dogs and cats. Adipose tissue collected from young dogs and cats undergoing spaying and neutering will produce a higher level of stem cells. Such cells can be used, e.g., for "banking" the cells for subsequent return to the patient or in the allogeneic treatment of another animal.

A tissue is processed to release cells from other tissue components by any of a variety of different means or combinations thereof. In many embodiments, tissue is physically processed, e.g., by cutting or mincing a tissue sample into smaller pieces. In certain embodiments, tissue is processed by exposure to an enzyme preparation that facilitates the release of cells from other tissue components, while in other embodiments, the processing of tissue does not include exposure to an enzyme that facilitates the release of cells from other tissue components. In one embodiment, the enzyme preparation is a collagenase preparation or comprises collagenase. In related embodiments, the enzyme preparation comprises one or more of trypsin-like, pepsin-like, clostripain, and neutral protease-type enzymes. Typically, the methods of the invention include processing by one or more of the following procedures: physical cutting, enzymatic treatment, ultrasonic energy treatment, and perfluorocarbon treatment.

In one embodiment, the processing of a tissue comprises physically cutting the tissue into smaller pieces. Cutting may be performed by any means available, including, e.g., the use of scissors, scalpels, razor blades, needles, and other sharp instruments.

In one embodiment, physical cutting of a sample is performed using a device comprising an array of screens. A tissue sample is placed onto the array of screens, which are typically held within a container. The number of screens arrayed together to receive the adipose tissue is preferably sufficient to contain the volume of the tissue sample within the openings of the screens. In one embodiment, the screens comprise a sharp edge, which cuts the tissue sample as it is applied to the array of screens. In another embodiment, the device is constructed such that one or more of the screens can be separated from a neighboring screen, and a cutting device, such as a wire, blade, or scalpel may be passed or inserted between the screens to further process and cut the tissue. The screens themselves may be constructed from any suitable material, including, e.g., metal, ceramic, plastic or glass. In various embodiments, the container holding the screens comprises an opening through which the tissue sample may be applied to the screens.

Without wishing to be bound to any particular theory, it is understood that the tissue, e.g., adipose tissue, is dispersed on the openings of the screens and, therefore, has a more uniform particle distribution compared to the traditional use of scissors to mince the tissue into smaller particles. This method also avoids subjecting the tissue to high shear forces in order to produce smaller particles. The adipose tissue thus becomes dispersed into more uniformly sized particles that will be enzymatically modified at a uniform rate upon subsequent or concurrent enzymatic treatment. Such arrangement promotes a more rapid release of cells and, therefore, reduces the contact time between released cells and the enzyme solution. Moreover, using the inventive device and process, it also is possible to remove the free cells, since the residual tissue matrix is retained on the screens. Still further, and in contrast to heretofore known devices, it is possible to visually inspect the amount of tissue remaining on the screens, in order to assess the extent of the dissolution process and determine the point at which processing is completed. Consequently, this screen device and methods utilizing the device allow for more expeditious processing of tissue, since variability of the enzyme solution does not need to be determined before hand due to the ability to see the extent of the processing by observing the amount of tissue remaining on the screens.

In certain embodiments, processing of the tissue includes enzymatic treatment, as described, e.g., in Example 1. Typically, such enzymatic treatment involves exposing the tissue to one or more enzymes that facilitate the release of cells from other tissue components. Example of such enzymes include matrix metalloproteinases, clostripain, trypsin-like, pepsin-like, neutral protease-type and collagenases. Suitable proteolytic enzymes are described in U.S. Pat. Nos. 5,079,160; 6,589,728; 5,422,261; 5,424,208; and 5,322,790. In one embodiment, a tissue sample is exposed to collagenase at a concentration in a range of 0.01 to 10.0 mg/ml, 0.05 to 10 mg/ml, 0.5 to 2.5 mg/ml, or 0.75 to 2.0 mg/ml, for a time sufficient to release cells from other tissue components. In a related embodiment, the level of collagenase is 0.75 mg/ml (0.075%). The actual usage level may be routinely determined by the skilled artisan for the particular tissue type being digested, and it is further understood that the concentration may vary depending upon the particular source of the enzyme. In particular embodiments, collagenase is used at approximately 0.75 or 0.9 mg/ml (Sigma-Aldrich, Cat. #2674), or 0.75 or 2.0 mg/ml (Serva NB4). Enzymatic treatment may be performed at a variety of different temperatures and time durations, which are understood generally to be inversely correlated to some degree. For example, in one embodiment, collagenase treatment is performed at 37° C. for 2-5 minutes multiple times (with removal of cells after each time period) or as long as 3-4 hours. In one embodiment, the total incubation with enzyme is 20-60 minutes.

In one embodiment, ultrasonic energy is used to process a tissue sample. In a specific embodiment, a transducer is applied to a fluid filled chamber containing the tissue being processed. The energy is applied and dissolution of the tissue occurs. In related embodiment, this procedure is performed separately or in combination with enzymatic treatment. Conditions of the ultrasonic treatment are selected so that adipose tissue is affected without the cells therein being significantly damaged. The use of ultrasonic energy has previously been shown to improve the dissolution of adipose tissue under in vivo procedures relating to lipoaspiration and suitable conditions for in vivo dissolution of adipose tissue have been described in US Patent Application Publication No. 2002/0128592 A1, which conditions may be adapted for the in vitro uses described herein.

In another embodiment, processing of a tissue sample includes treatment with a medically-compatible perflurocarbon solution, e.g., as described in Example 2. Typically, the adipose tissue is placed into contact with or mixed with the perflurocarbon solution for sufficient time to generate an emulsion. The perflurocarbon solution layer is then aspirated, leaving the aqueous layer containing the stem cells. The use of medically-compatible compositions of perflurocarbons has been reported to aid in the in vivo removal of adipose tissue performed on human subjects (see, e.g., U.S. Pat. No. 6,302,863), and methods and perflurocarbon solutions described therein may be applied to the in vitro methods of the present invention.

In various embodiments, released cells are purified from other tissue components after or concurrent with the processing of a tissue sample. As used herein, purification of cells means the release of cells from their normal tissue environment and does not indicate that the cells are purified or isolated from all other tissue components. In certain embodiments, purification of cells comprises separating cells from certain insoluble tissue components, including residual tissue material, such as lipids. Cells are separated from other tissue components by any means known and available in the art, including, e.g., the use of density gradients, centrifugation, and filtration or combinations thereof. Example of specific methods of purifying cells are known and described in the art, e.g., in U.S. Pat. No. 6,777,231. In certain embodiments, negative separation methods are employed to remove one or more particular types of cells.

Cells prepared according to the methods of the invention may be used immediately or stored prior to use. In certain embodiments, cells are isolated from a tissue sample at a geographic location different from the location where the tissue sample was obtained or where the tissue sample is to be provided to a patient. In such circumstances, the purified cells are typically stored prior to shipment to a physician or veterinarian for administration to a patient. The cells may be stored temporarily at approximately 4° C., or the cells may be frozen under liquid nitrogen for long term storage. A variety of methods of freezing cells for long term storage and recovery are known in the art and may be used according to the invention, including freezing cells in a medium comprising fetal bovine serum and dimethylsulfoxide (DMSO), as exemplified in Example 7.

In certain embodiments, purified cells, whether previously frozen or not, are placed into a vehicle suitable for administration. For example, purified cells may be placed into a syringe suitable for injection into a patient at a wound site or via intravenous administration.

Remarkably, it was discovered according to the invention that purified cell populations retained viability over time, when stored under refrigeration, e.g., at temperatures less than 12°, or while shipped on cold packs. This discovery was particularly surprising, since it had previously been shown that the use of enzymatic treatments like collagenase reduce the viability of cells, due to degradation of membrane structures (Brundstedt, J. et al., Methods in Diabetes Research, V. 1, Laboratory Methods, Lamer, J. and Pohl, S. L. (eds.), Wiley-Interscience, New York, 1985), and the prior understanding in the art was that purified stem cell populations could not be stored without substantial loss of viability unless specific steps were taken to preserve viability, including addition of proteins, nutrients, serum and tissue culture media of a variety of compositions.

Accordingly, in another embodiment, the invention provides a purified cell population comprising stem cells useful in the treatment and prevention of injury and disease, which can be stored at a temperature of less than 12° C. and transported under refrigeration or in the presence of cold packs prior to delivery to a patient. Such stem cell populations and compositions may be used in procedures providing purified stem cells for therapeutic or prophylactic purposes.

In certain embodiments, such cell populations are prepared according to a method of the present invention. However, in other embodiments, the cell populations may be isolated by any other means in the art, including those methods that employ enzymatic treatment and those that do not. In one embodiment, the cell populations and related methods include a step of culturing or rinsing the cells in the presence of serum or nutrient buffers, which can inhibit collagenase activity due to serum components.

The invention also includes methods of providing a stem cell population that may be transported under refrigeration or on cold packs to a location other than where the stem cell population was prepared. In one embodiment of such a procedure, a tissue sample is obtained from a patient by a physician or veterinarian and shipped to a laboratory. At the laboratory, the sample is processed to provide a purified cell population comprising stem cells. The purified cell population, or a portion thereof, is then shipped to a physician or veterinarian and subsequently delivered to the patient. The purified cells may be stored prior to shipment, e.g., at 4° C. or under liquid nitrogen. In one embodiment, the purified cell population is transferred to and shipped in a vehicle, such as a syringe, suitable for delivering the cell population to a patient. In particular embodiments, the cells are stored cold, i.e. less than 12° C. for 24 hours or 48 hours without losing significant viability or losing less than 5%, 10%, 20%, or 50% viability.

The current invention may be further applied industrially as a method of providing a medical service. Thus, in one embodiment, the invention includes a method of providing purified stem cells, comprising providing a kit for obtaining a tissue sample from a patient to a physician or veterinarian, processing the obtained tissue sample to purify a cell population comprising stem cells, and shipping a purified cell population to a physician or veterinarian in a device suitable for administering the cell population to a patient. These methods permit such off-site processing, since they provide a stem cell population having a high percentage of viable cells even after storage and shipment at less than 12° C. or on ice. Of course, it is understood that the method may be modified without falling without the scope of the present invention. For example, in one embodiment, the method may not include the step of providing a kit for obtaining a tissue sample, since the physician or veterinarian can usually obtain and ship a tissue sample to a laboratory for processing using materials at hand. Furthermore, it is not necessary according to the method for the cells to be shipped in a device suitable for administration to a patient. Rather, the cells may be shipped in a container, e.g., a vial, and subsequently transferred into a device suitable for administration.

In one specific embodiment, a sample of adipose tissue obtained from a horse by a veterinarian is processed according to a method of the invention, and the purified stem cell population is placed into a syringe and shipped on cold packs to the veterinarian. The purified stem cell population may then be provided to a site of injury or potential injury in the horse from which the tissue sample was obtained. In particular embodiments, the site of injury is a tendon, ligament, cartilage or bone, including, e.g., a strain or fracture.

B. Compositions and Kits Comprising Purified Stem Cells

The method of the invention results in a purified cell population having a unique composition that has distinct advantages in the treatment and prevention of injuries. The cell population purified according to the methods of the invention includes multipotent stem cells, such as e.g., mesenchymal or embryonic stem cells. However, as used herein, the term "purifed" does not indicate the presence of only stem cells. Rather, the term "purified" indicates that the cells are removed from their natural tissue environment and are present at a higher concentration as compared to the normal tissue environment. Accordingly, a "purified" cell population may further include cell types in addition to stem cells and may include additional tissue components. In particular embodiments, purified cell populations comprise at least 10,000, 20,000, 50,000, 100,000, 200,000, 500,000, 600,000, 700,000, 800,000, 900,000, $1 \times 10^6$, $2 \times 10^6$, $3 \times 10^6$, $5 \times 10^6$, or $10 \times 10^6$ cells per gram of tissue. In certain embodiments, at least 600,000 to $70 \times 10^6$ cells are isolated from 3 to 50 grams of tissue. In related embodiments, the purified cells are present at a concentration approximately 40 to 50-fold greater than their concentration in the tissue from which they were isolated, when initially pelleted.

In certain embodiments, a stem cell is of mesodermal origin. Typically, such stem cells retain two or more mesodermal or mesenchymal developmental phenotypes. In particular, such cells have the capacity to develop into mesodermal tissues, such as mature adipose tissue, bone, various tissues of the heart, dermal connective tissue, hemangial tissues, muscle tissues, urogenital tissues, pleural and peritoneal tissues, viscera, mesodermal glandular tissue and stromal tissue. In other embodiment, a stem cell has the capacity to develop into neural ectodermal tissue.

The purified cells demonstrate a high degree of viability, both before and after storage at 4° C. or under liquid nitrogen, and after being shipped at temperatures less than 12° C. or on ice. In certain embodiments, the percentage of viable cells, as determined by standard Trypan blue dye exclusion methods, immediately following preparation of a tissue sample is at least 50%, 60%, 70%, 80% or 90%. In related embodiments, the percentage of viable cells, as determined by standard Trypan blue dye exclusion methods, following storage at 4° C. for 24 hours or storage under liquid nitrogen for two weeks is at least 40%, 50%, 60%, 70%, 80% or 90%. In another embodiment, the percentage of viable cells, as determined by standard Trypan blue dye exclusion methods, following refrigerated storage or shipment on ice packs for less than 24 hours is at least 30%, 40%, 50%, 60%, 70%, 80% or 90%.

In addition, in certain embodiments, the cell populations also include other cell types, such as one or more of the following: red blood cells, white blood cells, neutrophils, monocyte/macrophages, fibroblasts, fibroblast-like cells, lymphocytes, and basophils. However, in certain embodiments, the compositions and cell populations do not include lymphocytes (i.e., T or B cells) or have a significantly reduced percentage of lymphocytes as compared to the amount present in peripheral blood. In specific embodiments, the percent of total cells in the purified cell population that are lymphocytes is reduced by at least 50%, 60%, 70%, 80%, 90%, 95%, 99% or 100% as compared to the percent of total cells in the original tissue sample that are lymphocytes. In related embodiments, lymphocytes represent less than 1%, 2%, 5%, 10%, 20%, 30%, 40%, or 50% of the total cells present in the purified cell population. In particular embodiments, the purified cell population does not comprise an appreciable number of lymphocytes. An appreciable number of lympocytes, as used herein, refers to at least 5% of the cell population being lymphocytes. Since the methods of the invention do not typically include a step of separating stem cells from other purified cells, these additional cells may be present in the originally purified cell population. Alternatively, non-stem cells may be added to the purified cell population at any time prior to administration to a patient.

In further embodiments, the cell populations also include non-cellular tissue components. Such non-cellular components may be soluble factors, or, alternatively, they may be insoluble components, such as lipids, or both. Examples of such non-cellular tissue components include extracellular matrix proteins, proteoglycans, secreted factors, cytokines, growth factors, differentiation-inducing factors, and differentiation-inhibiting factors, or fragments thereof. In one embodiment, the cell populations include collagen, thrombospondin, fibronectin, vitronectin, laminin, or fragments thereof. In a particular embodiment, the cell populations include collagen or fragments thereof. Collagens include, but are not limited to, Type I, Type II, Type III, and Type IV collagen. Again, these additional non-cell components frequently will be present in the originally isolated cell population. However, in certain embodiments, such non-cell components are added to the purified cell population prior to administration to a patient.

Without wishing to be bound to any particular theory, it is understood that the presence of tissue components in addition to stem cells provides a therapeutic advantage over stem cell populations lacking other tissue components, e.g., by providing additional factors that promote appropriate differentiation of the stem cells upon administration to a patient and/or possess. In addition, certain components are understood to possess intrinsic wound healing and preventative properties and, thus, cooperate with the stem cells in tissue repair and wound prevention.

In certain embodiments, the purified cell populations are present within a composition adapted for and suitable for delivery to a patient, i.e., physiologically compatible. Accordingly, compositions of the stem cell populations will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives.

In other embodiments, the purified cell populations are present within a composition adapted for or suitable for freezing or storage, such as the freezing medium described in Example 7.

The methods and compositions of the present invention are particularly well-adapted to being practiced using a kit, since they permit the storage and shipment of stem cell populations. In certain embodiments, a kit comprises a device suitable for administering the purified stem cell composition to a patient and containing an amount of stem cell composition to be administered. In one embodiment, a kit useful in the treatment of a musculo-skeletal tissue injury in an animal comprises a syringe containing a composition comprising purified adipose tissue-derived stem cells obtained from the animal in a physiologically compatible solution. It is understood that a kit may include any of the purified stem cell populations and compositions described herein. Accordingly, kits of the invention may be prepared for autologous, allogeneic or xenogeneic administration, and may further comprise additional tissue components (cellular or non-cellular) that are co-purified with the stem cells or added to the composition after purification of the stem cells.

C. Methods of Treating and Preventing Injury

In certain embodiment, the purified stem cells and compositions comprising the same are used to treat a clinically obvious injury or disease in a patient. In other embodiment, they are used prophylactically to prevent sub-clinically non-obvious injury or disease. In addition, in certain embodiments, they are used autologously to treat a patient from which the purified stem cells were isolated, while in other embodiments, they are used allogeneically to treat a patient other than the donor from which the stem cells were purified. In one embodiment, they are used to treat a patient of the same species, while in another embodiment, they are used to treat a patient of a difference species, i.e., xenogeneic.

In certain embodiments, the purified stem cells and related compositions are used to treat a variety of different diseases, including but not limited to inflammatory diseases, cardiovascular diseases, nervous system diseases, tumors, demyelinating diseases, digestive system diseases, endocrine system diseases, reproductive system diseases, hemic and lymphatic diseases, immunological diseases, mental disorders, musculoskeletal diseases, neuromuscular diseases, metabolic diseases, skin and connective tissue diseases, urological diseases.

In various embodiments, the purified stem cells and related compositions are used to treat a variety of different wounds, including but not limited to, abrasions, avulsions, blowing wounds, incised wounds, burns, contusions, puncture wounds, surgical wounds and subcutaneous wounds.

In particular embodiments, the purified stem cells and related compositions are used to treat or prevent a variety of injuries, including but not limited to, injuries to muscle, connective tissue (including tendon, ligament and cartilage), bone, hoof laminae, lung tissue, blood vessels, nerve, liver, musculo-skeletal tissue or cardiac tissue. In particular embodiments, the injury is a sports related injury, which includes but is not limited to contusions, myositis, strains, (including muscle and tendon strains), microtears, fractures (including avulsion fractures), dislocation, tear, sprains, stress fractures, bursitis, and articular cartilage injury.

In one embodiment, the injury is an injury associated with a performance animal, such as a tendon or ligament injury, which are frequently observed in competitive or racing mammals such as humans, horses, dogs and camels. In one embodiment, the injury occurs in a horse or camel within a superficial digital flexor tendon, suspensory ligament, accessory ligament of the deep digital flexor tendon, menisci, or other ligament such as cruciate ligaments. In another embodiment, the injury occurs in a dog within an Achilles tendon, cruciate ligament, meniscus, or flexor tendon. In certain embodiments wherein the patient is a human, the injury is of the Achilles tendon, quadriceps tendon, rotator cuff, lateral or medial epichondylitis, cruciate ligament, intervertebral disc or meniscus. Accordingly, in related embodiments, examples of particular injuries include tendonitis, tendinopathy, desmitis, bowed tendon, fractures, and strains.

Cell populations and related compositions may be provided to a patient by a variety of different means. In certain embodiments, they are provided locally, e.g., to a site of actual or potential injury. In one embodiment, they are provided using a syringe to inject the compositions at a site of possible or actual injury or disease. In other embodiments, they are provided systemically. In one embodiment, they are administered to the bloodstream intravenously or intra-arterially. The particular route of administration will depend, in large part, upon the location and nature of the disease or injury being treated or prevented. Accordingly, the invention includes providing a cell population or composition of the invention via any known and available method or route, including but not limited to oral, parenteral, intravenous, intra-arterial, intranasal, and intramuscular administration.

In one specific embodiment, a method of treatment comprises injecting a composition comprising stem cells isolated from an adipose tissue sample obtained from the tail head region of a horse and prepared according to a method of the invention into the same horse at a site of actual or potential injury, such as a tendon or ligament.

The development of suitable dosing and treatment regimens for using the cell populations and compositions described herein in a variety of treatment regimens, including e.g., oral, parenteral, intravenous, intranasal, and intramuscular administration and formulation, will again be driven in large part by the disease or injury being treated or prevented and the route of administration. The determination of suitable dosages and treatment regimens may be readily accomplished based upon information generally known in the art.

Treatment may comprise a single treatment or multiple treatments. In particular, for preventative purposes, it is contemplated in certain embodiments that purified cell populations of the invention are administered prior to a stress that might potentially cause injury, such as, e.g., an animal race (e.g., dog or horse race).

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

Example 1

Preparation of Adipose-Tissue Derived Stem Cells Using Enzymatic Degradation

Stem cells from adipose tissue obtained from four equines were prepared according to the following procedure, and the number and viability of purified cells was determined.

a. Label processing tubes (50 ml conicals). Determine the weight of each conical, record on the label.
b. Transfer fat sample to the inside surface of a lid from a Petri dish. Allow to drain.
c. Place fat sample in pre-weighed conical tube.
d. Record weight of fat sample and tube.
e. Add 30-40 ml of sterile PBS to the conical, cap and gently invert several times.
f. Carefully pour off liquid by using sterile forceps to retain the fat.
g. Transfer fat to the bottom portion of a sterile petri dish and mince with scissors and forceps.
h. Return minced sample to original 50 ml conical by using sterile scoop.
i. Rinse the petri dish with 15 ml of sterile PBS to dislodge any remaining fat particles and pour liquid/particles into the conical.
j. Carefully aspirate PBS from the tube until approximately 5 ml of PBS remains.
k. Prepare the required amount of collagenase solution by determining the volume of the fat present in the conical. Make sufficient volume of collagenase to equal 1.1× the volume of fat to be treated. Collagenase stock is 0.075% in PBS (i.e., 75 mg per 100 ml). Filter sterilize the collagenase stock solution by using a 0.22 µm sterile filter. Place collagenase stock solution in a 37° C. water bath.
l. Add enough sterile PBS to bring level to 40-45 ml mark, then cap.
m. Mix by inverting several times.
n. Aspirate the aqueous layer present, leaving 5 ml of volume.
o. Repeat Steps 21-2n until aqueous layer is relatively clear of debris/blood (e.g., 2× or 3×, depending on how bloody the sample is).
p. After final aspiration, add collagenase enzyme solution (warmed to 37° C.). Mix well. Add a volume of collagenase stock solution equal to the total volume of the minced fat sample (fat and residual PBS).
q. Incubate tubes in 37° C. water bath with agitation for 20-60 minutes, depending on the rate of fat degradation.
r. Dry tubes and spray outside of tubes with 70% Isopropyl alcohol.
s. Add enzyme-neutralizing solution (optional, based on adding DMEM with FCS).
t. Centrifuge tube at 400×g for 5 minutes, swinging bucket rotor (set at 4° C.).
u. Aspirate/pour off supernatant, removing fat layer.
v. Resuspend pellet by gently "flicking" the bottom of the tube with a finger.
w. Add 10 ml of PBS and mix gently by inversion.
x. Pour resuspended cells through tissue filter (e.g., 70 µm) into a labeled 50 ml conical tube to remove any tissue matrix and debris. After the suspension has drained into the conical, gently rinse the tissue filter with approximately 20 ml of sterile PBS, collecting the rinsate in the conical (including the underside of the filter unit itself).
y. Centrifuge the tube at 400×g for 5 minutes, swinging bucket rotor.
z. Aspirate/pour off supernatant.
aa. Resuspend cell pellet in a small volume of medium.
bb. Transfer 50 µl of each sample to the appropriate labeled 0.5 ml plastic tube for cell counting and viability determination.

Cell count and viability determinations were performed according to the following procedures.

a. Add 50 µl of 0.4% Trypan Blue dye exclusion medium to the tube in Step bb.
b. Mix gently and allow to stand for 1-2 minutes.
c. Load one chamber of the hemacytometer with a sample. Let sit for 1-2 minutes.
d. Perform cell count and viability determination by counting at least 100 cells (but fewer than 500 cells) contained in the 4 large grid areas.
e. Perform calculations of cell number and viability.

The results of these experiments are shown in Table 1, which provides the number of cells isolated per gram of adipose tissue and the percent viability of cells from each sample.

TABLE 1

Viability and number of adipose tissue-derived cells

| Sample Number | % Viability | Cell Number/g of adipose tissue |
|---|---|---|
| 1 | 68.5 | $0.86 \times 10^6$ |
| 2 | 55.7 | $0.91 \times 10^6$ |
| 3 | 72.0 | $0.36 \times 10^6$ |
| 4 | 75.4 | $0.35 \times 10^6$ |

These experiments demonstrate that the procedure of the present invention provides a remarkably high number of viable cells per gram of tissue and is, therefore, extremely useful for preparing stem cells for therapeutic and prophylactic treatments.

Example 2

Preparation of Adipose-Tissue Derived Stem Cells Using Perflurocarbons to Release Stem Cells from Tissue The following procedure for preparing adipose-tissue derived stem cells is adapted from the procedure of Example 1 by the addition of treatment with perflurocarbons to assist in the release of stem cells from adipose tissue.

a. Label processing tubes (50 ml conicals). Determine the weight of each conical, record on the label.
b. Transfer fat sample to the inside surface of a lid from a Petri dish. Allow to drain.
c. Place fat sample in pre-weighed conical tube.
d. Record weight of fat sample and tube.
e. Add 30-40 ml of sterile PBS (with a pH of 6.9; to be used throughout the procedure) to the conical, cap and gently invert several times.
f. Carefully pour off liquid by using sterile forceps to retain the fat.
g. Transfer fat to the bottom portion of a sterile Petri dish and mince with scissors and forceps.
h. Return minced sample to original 50 ml conical by using sterile scoop.
i. Rinse the Petri dish with 15 ml of sterile PBS to dislodge any remaining fat particles and pour liquid/particles into the conical.
j. Carefully aspirate PBS from the tube until approximately 5 ml of PBS remains.
k. Add an amount of perflurocarbon solution equal to the volume of the adipose sample, including PBS. Shake to bring the adipose tissue into contact with the perflurocarbon solution. Use of a "rocker" platform will aid in this procedure. At completion, aspirate the PFC layer without removing the aqueous layer.
l. Prepare the required amount of collagenase solution by determining the volume of the fat present in the conical. Make sufficient volume of collagenase to equal 1.1× the volume of fat to be treated. Collagenase stock is 0.075% in PBS (i.e., 75 mg per 100 ml). Filter sterilize the collagenase stock solution by using a 0.22 µm sterile filter. Place collagenase stock solution in a 28° C. water bath.
m. Add enough sterile PBS to bring level to 40-45 ml mark, then cap.
n. Mix by inverting several times.
o. Aspirate aqueous layer, leaving 5 ml of volume.
p. Repeat Steps 21-2n until aqueous layer is relatively clear of debris/blood (e.g., 2× or 3×, depending on how bloody the sample is).
q. After final aspiration, add collagenase enzyme solution (warmed to 37° C.). Mix well. Add a volume of collagenase stock solution equal to the total volume of the minced fat sample (fat and residual PBS).
r. Incubate tubes in 37° C. water bath with agitation for 20-60 minutes, depending on the rate of fat degradation.
s. Dry tubes and spray outside of tubes with 70% Isopropyl alcohol.
t. Add enzyme-neutralizing solution (optional, based on adding DMEM with FCS).
u. Centrifuge tube at 400×g for 5 minutes, swinging bucket rotor (set at 4° C.).
v. Aspirate/pour off supernatant, removing fat layer.
w. Resuspend pellet by gently "flicking" the bottom of the tube with a finger.
x. Add 10 ml of PBS and mix gently by inversion.
y. Pour resuspended cells through tissue filter (70 µm) into a labeled 50 ml conical tube to remove any tissue matrix and debris. After the suspension has drained into the conical tube, gently rinse the tissue filter with approximately 20 ml of sterile PBS, collecting the rinsate in the conical (including the underside of the filter unit itself).
z. Centrifuge the tube at 400×g for 5 minutes, swinging bucket rotor.
aa. Aspirate/pour off supernatant.
bb. Resuspend cell pellet in a small volume of medium.
cc. Transfer 50 µl of each sample to the appropriate labeled 0.5 ml plastic tube for cell counting and viability determination.

Example 3

Isolation of Stem Cells from Adipose Tissue Obtained from the Tail Head Region of a Horse The optimal location on a horse for the collection of an adipose tissue sample for isolation of stem cells is not readily apparent, since fat is deposited at numerous sites in horses. The system of body condition scoring (Ott E A. Chairman Subcommittee on horse nutrition: Nutritional Requirement of Horses. 5$^{th}$ ed National Academy Press, Washington D.C. (1989)) describes fat accumulating in numerous locations on the horse.

To determine if the tail head region is a preferred location for collecting fat tissue, a number of adipose tissue samples were obtained from both thin and fat horses and processed as described in Example 1. Specifically, samples were obtained from the tail head region of four equine patients and the neck of one equine patient. The processed samples were analyzed to determine viability and number of stem cells, and the results are provided in Table 2. Adherent cells were observed for selected samples that were cultured, indicating the presence of viable stem cells.

TABLE 2

Viability and Number of Cells Obtained from the Tail Head Region

| Sample # | Location | % Viability | Cell Number/g of adipose tissue |
|---|---|---|---|
| 1 | Tail Head | 68.5 | $0.86 \times 10^6$ |
| 2 | Tail Head | 55.7 | $0.91 \times 10$ |
| 3 | Tail Head | 72.0 | $0.36 \times 10^6$ |
| 4 | Tail Head | 75.4 | $0.35 \times 10^6$ |
| 5 | Neck | N/A | No cells isolated |

The results of these experiments establish that the tail head region is a preferred location to obtain adipose tissue from a horse. Adipose tissue derived from the tail head region provided increased number of cells as compared to adipose tissue derived from the neck. The tail head region also offers additional advantages as compared to other locations, including greater ease of access and safety in a chute or stanchion, no requirement for general anesthesia, no significant nerves or vessels are located in this area, and fat is available in adequate amounts for collection and is close to the body surface. In addition, the surprising finding was made that the tail head area is one of the few areas where fat is located distinct from other fibrous tissues.

Example 4

Small animals, including dogs and cats, possess a number of potential anatomical sites for obtaining adipose tissue. Stem cells were isolated from adipose tissue obtained from a variety of anatomical sites in animals according to the procedure described in Example 1, and the amount of cells isolated and their viability was determined. The results are shown in Table 3.

TABLE 3

Viability and Number of Cells Obtained from Small Animals

| Identification No. | Species | Sample Type | % Viability | Viable Cells/gram Adipose Tissue |
|---|---|---|---|---|
| 061302-01 | Feline | Lipoaspirate | 85.0 | N/A |
| 061302-02 | Canine | Lipoaspirate | 77.0 | N/A |
| 061902-01 | Feline | Lipectomy | 89.4 | $2.85 \times 10^6$ (total) |
| 071202-01 | Canine | Lipectomy | 97.1 | $1.12 \times 10^6$ (total) |
| 110702-01 | Feline | Lipectomy | 94.4 | $0.61 \times 10^6$ |
| 092303-01 | Canine | Broad-Lig. | 86.5 | $2.3 \times 10^6$ |
| 092303-02 | Canine | Subcutaneous | 75.2 | $0.59 \times 10^6$ |
| 092303-03 | Canine | Omental | 55.2 | $1.1 \times 10^6$ |
| 092403-01 | Feline | Subcutaneous | 63.2 | $0.26 \times 10^6$ |
| 092403-04 | Feline | Omental | 66.7 | $0.30 \times 10^6$ |
| 092403-02 | Canine | Omental | 85.2 | $1.84 \times 10^6$ |
| 092403-03 | Feline | Subcutaneous | 91.7 | $0.8 \times 10^6$ |
| 092503-01 | Feline | Subcutaneous | 80.6 | $0.26 \times 10^6$ |
| 092503-02 | Feline | Omental | 77.0 | $0.51 \times 10^6$ |
| 092603-01 | Canine | Subcutaneous | 76.1 | $0.46 \times 10^6$ |
| 092603-02 | Canine | Omental | 90.3 | $1.57 \times 10^6$ |
| 100303-01 | Canine | Subcutaneous | 68.6 | N/A |
| 100303-02 | Canine | Omental | 67.0 | $0.21 \times 10^6$ |
| 100303-03 | Canine | Broad Lig. | 60.0 | $0.31 \times 10^6$ |
| 100303-04 | Canine | Broad Lig. | 67.0 | $0.22 \times 10^6$ |

These results demonstrate that viable stem cells may be isolated from a variety of different locations in small animals. In addition, they further establish that the procedures of the present invention result in the isolation of a surprisingly substantial number of viable cells and are, therefore, particularly well-suited for the preparation of stem cells for therapeutic and prophylactic treatment of patients, since a large number of viable cells may be isolated from a relatively small tissue sample.

Example 5

Preparation of Adipose Tissue-Derived Stem Cells Using a Module for Tissue Processing Adipose tissue obtained from a patient by standard methods (e.g., lipectomy, lipoaspiration, or other suitable procedure) is brought into contact with a series of screens within a module and is forced into the mesh of the screens. Once the adipose tissue has been dispersed throughout the screens, the individual screens are separated slightly from their neighbors, creating a gap between the screens. The screens are moved in a parallel manner relative to one another, or a thin blade may be passed between adjacent screens in order to obtain discretely distributed adipose tissue held within the openings of each screen.

The set of screens is processed individually or is maintained in a "block" arrangement. In either case, an enzymatic solution is added to the container in which the screens are placed and allowed to come into contact with the adherent adipose tissue. Free cells released from the screens are recovered, while the residual tissue matrix is retained on the screens.

Example 6

Isolation of Stem Cells Using Adherent Material

Stem cells were isolated from adipose tissue using small adherent materials, e.g., packing peanuts or Velcro pieces, to which the adipose tissue adheres, according to the following procedure. The effect of including either of these adherent materials in samples being processed was determined by monitoring their effect on filtration rates, as described below.

a. Packing peanuts were "chopped" with a vegetable chopper and scissors to reduce their nominal size to between 1 mm to 10 mm in diameter approximately.

b. The chopped peanuts were placed in a beaker and water was added. Only those peanuts that appeared to be within the dimensional range and floated were recovered.

c. Velcro was cut into pieces, essentially creating shreds of Velcro approximately 2-4 mm wide and the length of the original Velcro strip width. These shreds were placed in water to see if they floated.

d. The chopped peanuts (approx. 1 gram) were placed in the top of a Corning 115 mL filtration system and 100 mL of water was added. Vacuum was applied and the time that it took to filter the 100 mL was determined. As a control, the time to filter 100 mL of water by itself was measured.

e. In a fresh filtration device, the time to filter 100 mL of water in the presence of the shredded Velcro (approx. 1 gram) was determined.

f. 20 g of fat was minced as described in Example 1. The minced tissue was placed in a fresh Corning 115 mL filtration device. 100 mL of water was added, the fat particles were dispersed. Vacuum was applied and the time to filter was determined.

g. 20 g of fat was minced as described in Example 1. The minced tissue was mixed with the chopped peanuts and placed in a fresh Corning 115 mL filtration device. 100 mL of water was added and the particles were dispersed. Vacuum was applied and the time to filter the 100 mL of water was determined.

h. 20 g of fat was minced per the standard protocol. The shredded Velcro pieces were mixed with the fat and placed in a fresh Corning 115 mL filtration system. 100 mL of water was added and the particles were dispersed. Vacuum was applied and the time to filter the 100 mL of water was determined.

Most of the Velcro pieces and all of the minced packing peanut pieces floated in water. The time for 100 mL of water to filter in a filter system was recorded, along with the time it took for 100 mL of water to filter in the same filter unit in the presence of either the Velcro or packing peanut pieces. The final filtration assessment was determined with the fat tissue added directly to the filter or added to the filter after being mixed with the Velcro or packing peanut pieces. The fat coated both the Velcro and the packing peanuts quite well without extensive mixing being required, and it appeared that nearly all of the minced fat was in contact with the Velcro or packing peanut pieces. The initial filtration results are shown in Table 4.

TABLE 4

Filtration Times of Adipose Tissue Samples in the Presence or Absence of Adherent Materials

| Filter Unit | Condition | Time to Filter (sec) |
|---|---|---|
| 1 | $H_2O$ | 25 |
|   | $H_2O$/Velcro | 25 |
|   | $H_2O$/Velcro/Fat (20.361 g) | 39 |
| 2 | $H_2O$ | 24 |
|   | $H_2O$/Packing Peanuts | 25 |
|   | $H_2O$/Packing Peanuts/Fat (20.545 g) | 37 |
| 3 | $H_2O$ | 27 |
|   | $H_2O$/Fat (20.605 g) | 53 |

Additional filtration studies were performed using a 0.2 µm filter system from Nalgene. The previous assessment was made with a Corning filter system. Approximately 1 g of Velcro pieces and polystyrene packing peanut pieces were used in each of three filter units tested per condition. Fat without any agent present was used as the control. The time for 100 mL of water to filter in a filter system was assessed in the absence (control) or presence of either the Velcro/fat or packing peanut pieces/fat mixtures. The time for 100 mL of water to filter in a filter system was assessed in the absence (control) or presence of either the Velcro/fat or packing peanut pieces/fat mixtures. The time for 100 mL of water to filter was determined for each filter, after which the test condition was evaluated in the same filter. Approximately 20 g of fat was used per condition. The results are shown below in Table 5.

TABLE 5

Filtration Times of Adipose Tissue Samples in the Presence or Absence of Adherent Materials

| Filter Unit Number | Agent | Mass of Fat (g) | Time-to-Filter (sec) Water Only | Time-to-Filter (sec) Water/Fat/Agent |
|---|---|---|---|---|
| 1 | None | 20.156 | 24 | 44 |
| 2 | None | 20.176 | 23 | 48 |
| 3 | None | 20.511 | 23 | 51 |
| 4 | Velcro | 20.219 | 22 | 29 |
| 5 | Velcro | 20.373 | 22 | 30 |
| 6 | Velcro | 20.392 | 21 | 29 |
| 7 | Polystrene Peanuts | 20.051 | 23 | 40 |
| 8 | Polystrene Peanuts | 20.539 | 23 | 39 |
| 9 | Polystrene Peanuts | 20.534 | 20 | 34 |

The results shown above clearly demonstrate that the presence of either the Velcro or packing peanut pieces with the fat resulted in a substantial improvement in the filtration time. Filtration of untreated fat took almost twice as long compared to filtration of water alone, increasing from 27 seconds to 53 seconds upon the addition of the fat. However, filtration of fat mixed with the Velcro or packing peanut pieces only took approximately 1.5 times as long compared to filtration of water alone. These results indicate that the binding of the fat to the adherent material results in the generation of aggregates of adherent material/fat, which facilitates further processing.

Based on the observations made about the interaction of Velcro pieces with adipose tissue and the improved filtration that resulted from mixing the two together, an experimental assessment of the impact of including Velcro pieces present in the tissue processing procedure of Example 1 was performed as described below.

Approximately 1 g of Velcro pieces that had been washed with water and then dried was mixed with approximately 10.5 g of adipose tissue. A control lacking Velcro pieces was performed with 10.9 g of adipose tissue. The test materials were processed essentially according to the protocol in Example 1. Cell count and viability assays were performed at the end of the process, and the results are shown in Table 6.

TABLE 6

Stem Cell Viability and Cell Number When Processed Using Velcro Pieces

| Condition | Viability (%) | Cells/g | Cell Yield |
|---|---|---|---|
| No Velcro | 62.5 | 20,000 | 220,000 |
| Velcro | 62.6 | 60,000 | 660,000 |

These results demonstrate that including small adherent materials during tissue processing results in an increased cell yield with comparable viability. Accordingly, the addition of small adherent materials during tissue processing provides a remarkably superior method for preparing stem cells, since it provides the substantial advantage of requiring less tissue to yield the same number of cells.

Example 7

Method of Freezing Purified Stem Cells

Purified cell populations are prepared for storage in liquid nitrogen according to the following procedure.

a. Freezing medium is prepared by determining the total number of cryovials to be used. Generally, this involves dividing the number of cells available by 3 million. Each cryovial receives 1.0 ml of freezing medium/cells, so the total number of cryovials is multiplied by 1.25 to determine the volume of freezing medium made. The appropriate number of cryovials is placed into a Cryo-Safe that has been stored at −10° C. overnight.

b. While working in the tissue culture hood, pipette the appropriate amount of DMSO and fetal bovine serum such that the final amount of DMSO in the freezing medium is 10% and the final amount of fetal bovine serum in the freezing medium is 90%. Mix well.

c. Process the freezing medium through a sterile, DMSO-compatible 0.2 µm filter into a sterile 50 ml conical tube. Place the tube in the refrigerator for at least 45 min.

d. Centrifuge the isolated cell preparation at 400×g for 10 min. Carefully pour off the supernatant and flick the tube to fluidize the cell pellet.

e. Add enough freezing medium to the conical tube to yield 1 ml for each cryovial. This is done by slowly adding the freezing medium over the course of 30-60 seconds, while swirling the suspension to ensure mixing.

f. Gently pipette the cells with the freezing medium in order to ensure that the cells are completely resuspended.

g. Place 1.0 ml of the cell suspension into each of the cryovials. Cap and immediately transfer the vials to a Mr. Frosty.

h. Immediately place the Mr. Frosty on the bottom shelf of a −80° C. freezer. Place a cryovial storage cane in the freezer.

i. After a minimum of four hours storage in the −80° C. freezer (not to exceed 20 hours), place the cryovials in the cane and immediately transfer the cane to a liquid nitrogen storage tank.

Cells frozen under liquid nitrogen are thawed as follows.

a. Recovery medium is made by combining the appropriate volume of autologous serum and Iscove's Modified Dulbecco's Medium (IMDM) to allow for a minimum of 1:10 dilution of the contents of the cryovial (usually 1.0 ml). To this volume, add 1.5 ml to determine the final volume of recovery medium that should be made. Preferably, the ratio is 1:15. The final recovery medium is 20% autologous serum and 80% IMDM by volume. Transfer the amount of recovery medium to be used for washing to a sterile 50 ml conical tube. Place both tubes of recovery medium in the refrigerator for a minimum of 30 min.

b. The cryovial is removed from the liquid nitrogen storage tank and immediately placed in contact with a 37° C. water bath. The threads of the vial should not be submerged below the surface of the water.

c. After approximately 2.5 min., the vial is examined to determine if the cells have thawed. Excess heating of the vial should be avoided.

d. As soon as the cells appear thawed, the outside of the vial is washed with 70% isopropyl alcohol and placed into a Cryo-Safe that was stored at −10° C. overnight.

e. The contents of the vial are immediately transferred to the 50 ml conical containing the washing recovery medium using a sterile pipette, and the suspension is gently mixed.

f. The cell suspension is centrifuged at 400×g for 6 min.

g. The supernatant is gently poured off and the tube is flicked to fluidize the cells.

h. Add 1.0 ml recovery medium to resuspend the cells. Very slowly pipette the cells up and down in the pipette to mix the cells. Transfer the cells to a cryovial stored in the Cryo-Safe.

i. A 30 μl aliquot of the cell suspension should be taken for determining the viability and cell count.

j. 40 μl of sterile ticarcillin stock solution (25 mg/ml) is added and mixed gently.

k. An 18 gauge needle attached to a sterile 1 ml syringe is used to draw the suspension into the syringe. Remove any trapped bubbles by gently tapping the barrel of the syringe.

l. Remove the needle and place the sterile syringe tip cap on the end of the syringe.

m. Place the syringe in the refrigerator.

Packages of cells are prepared for shipment to a physician or veterinarian as follows.

a. A label including identification information is attached to the syringe.

b. The syringe is wrapped in bubble wrap and placed in a shipping box with ice packs above and below the syringe.

c. Any remaining space in the box is filled with packing material, the lid is inserted, and the box is sealed.

The viability of cells frozen and thawed according to the procedure is greater than 65%, indicating that these procedures may be used successfully to store purified stem cells.

Example 8

Validation of Syringe Storage of Cells

The viability of cells obtained by the collagenase-based processing protocol described in Example 1 was further examined to determine the impact of placing cells in a syringe and shipping the syringe to the attending veterinarian for return to the patient. The viability of each cell preparation was determined on Day 0. An aliquot of each cell preparation was then placed in a syringe, which was placed in a package with frozen cold packs and left at room temperature for between 20-24 hours before viability was determined (Day 1). For a subset of cell preparations, a control aliquot was stored in a refrigerator in a plastic tube for viability determination on Day 1. "ND" indicates that the viability was not determined. The results of these studies are provided in Table 7.

TABLE 7

Viability of Stem Cell Preparation Stored in a Syringe

| | Viability | | |
|---|---|---|---|
| | Day 0 | Day 1 | |
| Patient Identification | Control (%) | Control (%) | Syringe (%) |
| 092403-01 | 63.2 | ND | 74.0 |
| 092403-02 | 85.2 | ND | 73.5 |
| 092403-03 | 91.7 | ND | 83.8 |
| 092403-04 | 66.7 | ND | 54.3 |
| 092503-01 | 80.6 | 80.0 | 88.2 |
| 092503-02 | 77.9 | 79.2 | 81.8 |
| 101003-01 | 83.5 | 71.6 | 74.0 |
| 101003-02 | 81.3 | 69.6 | 74.3 |

Surprisingly, these results demonstrate that the stem cell preparations exhibited little or no reduction in viability when stored in syringes on cold packs, thereby demonstrating that stem cell populations may be prepared and shipped, e.g., in a syringe, to a different location for administration to a patient.

Example 9

Adipose-Derived Pluripotent Stem Cells for Tendon Repair

To demonstrate the clinical efficacy of stem cells prepared according to the methods of the invention, as provided in Example 1, a double-blinded, placebo-controlled study was performed using four cell therapy treated and four placebo-treated control horses. Lesions were created with collagenase to mimic natural tendonitis, and autologous cell transplants were conducted 10 days after lesions were induced. Adipose tissue from the tail head area on each animal was processed with the collagenase-based processing protocol. The cell preparations for four of the horses were injected into the lesions, and saline was injected for the controls. Weekly ultrasounds were performed. The horses were sacrificed at six weeks post therapy, and the wound sites examined.

The results of these experiments demonstrate statistically significant improvements in the injuries treated with the stem cell preparations (treated) as compared to the controls. Specifically, inflammatory cell infiltrates were not observed in the treated animals, whereas slight to moderate inflammatory infiltrate was observed in the controls, thus demonstrating the anti-inflammatory effect of the cell preparations. The treated injuries exhibited significant improvement in architecture with uniform collagen fiber creation and significant improvement in the crimp observed under polarized light indicating normal cross-linking of collagen. In addition, the treated injuries showed statistically significant improvement in the cell treated group demonstrating the overall benefit in improved healing of the tendons. Also, the treated injuries demonstrated improved collagen fiber linearity, more normal tendon shape and sparse tenocyte density, reduced hemorrhage and swelling, more normal new vessel numbers, reduction in lesion size in cells in treated as compared to controls as a percent of starting lesion size (baseline). The lesions in cell treated horses had a lower grade for most of the study as compared to controls, despite starting at an equivalent (or higher) value, and an improved linear fiber pattern was seen.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of treating an injury or disease in a mammal, comprising providing to the mammal a cell population comprising adipose-tissue derived stem cells, wherein said cell population was prepared by a cell processing method comprising:
   (a) processing adipose tissue obtained from a mammal to release cells therein, wherein said processing releases cells and a fat layer; and
   (b) separating cells released in (a) from the fat layer; thereby preparing the cell population comprising adipose tissue-derived stem cells;
wherein said cell processing method does not include isolating stem cells separated in (b) from other cells separated in (b),
thereby treating the injury or disease in the mammal.

2. The method of claim 1, wherein the processing of (a) comprises one or more procedures selected from the group consisting of: physical cutting or mincing of the adipose tissue; treating the adipose tissue with an enzyme that facilitates the release of cells; exposing the adipose tissue to ultrasonic energy; and treating the adipose tissue with perfluorocarbons.

3. The method of claim 1, wherein the processing of (a) comprises physical cutting or mincing of the adipose tissue.

4. The method of claim 1, wherein the separating of (b) comprises one or more procedures selected from the group consisting of: use of a density gradient; centrifugation; and filtration.

5. The method of claim 1, wherein:
   the processing of (a) comprises one or more procedures selected from the group consisting of: physical cutting or mincing of the adipose tissue; treating the adipose tissue with an enzyme that facilitates the release of cells; exposing the adipose tissue to ultrasonic energy; and treating the adipose tissue with perfluorocarbons; and
   the separating of (b) comprises one or more procedures selected from the group consisting of: use of a density gradient; centrifugation; and filtration.

6. The method of claim 1, wherein the adipose tissue-derived stem cells are autologous to the mammal being treated.

7. The method of claim 1, wherein said cell population further comprises one or more cells selected from the group consisting of: red blood cells, white blood cells, fibroblasts, neutrophils, monocyte/macrophages, and basophils.

8. The method of claim 1, wherein said cell population further comprises one or more other tissue components.

9. The method of claim 8, wherein the one or more other tissue components comprise: extracellular matrix polypeptides, proteoglycans, lipids, cytokines, or growth factors.

10. The method of claim 1, wherein the disease or disorder is selected from the group consisting of: inflammatory diseases or disorders, cardiovascular diseases, nervous system diseases, tumors, demyelinating diseases, digestive system diseases, endocrine system diseases, reproductive system diseases, hemic and lymphatic diseases, immunological diseases, mental disorders, musculoskeletal diseases, neuromuscular diseases, metabolic diseases, skin and connective tissue diseases, and urological diseases.

11. The method of claim 1, wherein the injury is a wound selected from the group consisting of: abrasions, avulsions, blowing wounds, incised wounds, burns, contusions, puncture wounds, surgical wounds and subcutaneous wounds.

12. A method of treating a disease or disorder in a mammal, comprising:
   (a) preparing a cell population comprising adipose tissue-derived stem cells for introducing into a mammal by a method comprising:
      (i) processing adipose tissue obtained from a mammal to release cells therein, wherein the adipose tissue comprises stem cells, wherein said processing releases cells and a fat layer; and
      (ii) separating the cells released in (i) from the fat layer, wherein the preparing does not include isolating stem cells separated in (a)(ii) from other cells separated in (a)(ii), thereby preparing the cell population comprising adipose tissue-derived stem cells; and
   (b) providing the cell population of (a)(ii) to the mammal, thereby treating the disease of disorder in the mammal.

13. The method of claim 12, wherein the processing comprises one or more procedures selected from the group consisting of:
   physical cutting or mincing of the adipose tissue;
   treating the adipose tissue with an enzyme that facilitates the release of cells;
   exposing the adipose tissue to ultrasonic energy; and
   treating the adipose tissue with perfluorocarbons.

14. The method of claim 12, wherein the wherein the separating comprises one or more procedures selected from the group consisting of:
   use of a density gradient;
   centrifugation; and
   filtration.

15. The method of claim 12, wherein the adipose tissue-derived stem cells are autologous to the mammal being treated.

16. The method of claim 12, wherein the cell population further comprises one or more cells selected from the group consisting of: red blood cells, white blood cells, fibroblasts, neutrophils, monocyte/macrophages, and basophils.

17. The method of claim 12, wherein the cell population further comprises one or more other tissue components.

18. The method of claim 17, wherein the one or more other tissue components comprise: extracellular matrix polypeptides, proteoglycans, lipids, cytokines, or growth factors.

19. The method of claim 12, further comprising:
   (c) freezing the cell population in a physiologically compatible buffer before step (b).

20. The method of claim 12, further comprising:
   (c) suspending the cell population in a physiologically compatible buffer before step (b).

21. The method of claim 12, wherein the disease or disorder is selected from the group consisting of: inflammatory diseases or disorders, cardiovascular diseases, nervous system diseases, tumors, demyelinating diseases, digestive system diseases, endocrine system diseases, reproductive system diseases, hemic and lymphatic diseases, immunological diseases, mental disorders, musculoskeletal diseases, neuromuscular diseases, metabolic diseases, skin and connective tissue diseases, and urological diseases.

22. The method of claim 12, wherein the injury is a wound selected from the group consisting of: abrasions, avulsions, blowing wounds, incised wounds, burns, contusions, puncture wounds, surgical wounds and subcutaneous wounds.

23. The method of claim 12, wherein the disease or disorder is a musculoskeletal injury or disease.

24. The method of claim 23, wherein the musculoskeletal injury or disease is a sprain, strain, dislocation, bruising, tear, microtear, contusion, bursitis, tendonitis, articular cartilage injury or fracture in a tendon, ligament, cartilage, bone, or hoof laminae.

* * * * *